United States Patent [19]
Shaber et al.

[11] Patent Number: 6,121,251
[45] Date of Patent: *Sep. 19, 2000

[54] DIHYDROPYRIDAZINONES AND PYRIDAZINONES AND THEIR USE AS FUNGICIDES AND INSECTICIDES

[75] Inventors: Steven Howard Shaber, Horsham; Edward Michael Szapacs, Center Valley; Ronald Ross, Jamison, all of Pa.

[73] Assignee: Rohm and Haas Company, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/938,552

[22] Filed: Sep. 26, 1997

Related U.S. Application Data

[60] Provisional application No. 60/028,336, Oct. 11, 1996.

[51] Int. Cl.[7] .......................... A01N 43/58; A01N 55/10; C07D 237/14; C07D 237/16

[52] U.S. Cl. .......................... 514/63; 514/85; 514/236.5; 514/247; 514/252; 544/229; 544/232; 544/239; 544/240; 544/114; 544/238

[58] Field of Search .................................. 544/239, 240, 544/229, 232; 514/252, 247, 85, 63

[56] References Cited

U.S. PATENT DOCUMENTS

| | | | |
|---|---|---|---|
| 5,075,471 | 12/1991 | Michelotti et al. | 556/144 |
| 5,252,594 | 10/1993 | Shaber et al. | 514/383 |
| 5,552,409 | 9/1996 | Michelotti et al. | 514/307 |
| 5,631,254 | 5/1997 | Michellotti et al. | 544/239 |
| 5,635,494 | 6/1997 | Ross et al. | 544/239 |
| 5,763,440 | 6/1998 | Ross et al. | 544/239 |

FOREIGN PATENT DOCUMENTS

| | | |
|---|---|---|
| 0619301 A2 | 10/1994 | European Pat. Off. . |
| 0704430 A1 | 4/1996 | European Pat. Off. . |

*Primary Examiner*—Emily Bernhardt
*Attorney, Agent, or Firm*—Guy T. Donatiello; Thomas D. Rogerson

[57] ABSTRACT

Compounds with fungicidal and insecticidal properties having formula I

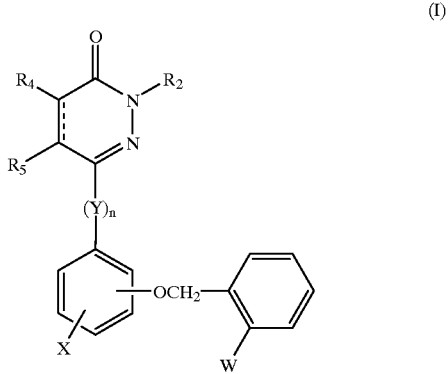

wherein W is

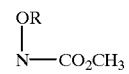

n is 0 or 1;

Y is O, S, $NR_1$, or $R_6$;

the ring bond containing $R_4$ and $R_5$ is a single or double bond;

X is independently selected from hydrogen, halo, $(C_1-C_4)$ alkyl, $(C_1-C_4)$alkoxy and —HC=CH—CH=CH— thereby forming a napthyl ring;

R is independently selected from $(C_1-C_{12})$alkyl and halo $(C_1-C_{12})$alkyl;

$R_1$ is independently selected from $(C_1-C_{12})$alkyl, $(C_2-C_8)$ alkenyl and aryl;

$R_2$ is independently selected from hydrogen, $(C_1-C_{12})$ alkyl $(C_1-C_{12})$alkoxy, halo$(C_1-C_{12})$alkyl, halo $(C_1-C_{12})$alkoxy, hydroxy$(C_1-C_{12})$alkyl, $(C_1-C_{12})$ alkoxy$(C_1-C_{12})$alkyl, $(C_1-C_{12})$alkoxycarbonyl $(C_1-C_{12})$alkyl, $(C_2-C_8)$alkenyl, halo$(C_2-C_8)$alkenyl, $(C_3-C_{10})$alkynyl, halo$(C_3-C_{10})$alkynyl, $(C_3-C_7)$ cycloalkyl, $(C_3-C_7)$cycloalkyl$(C_1-C_4)$alkyl, epoxy $(C_1-C_{12})$alkyl, $PO(OR_1)_2(C_1-C_{12})$alkyl, $R_1S(O)_2$ $(C_1-C_{12})$alkyl, $(R_1)_3Si(C_1-C_{12})$alkyl, aryl, aryloxy $(C_1-C_{12})$alkyl, arylcarbonyl$(C_1-C_{12})$alkyl, aralkyl, arylalkenyl, heterocyclic, heterocyclic $(C_1-C_{12})$alkyl, N-morpholino$(C_1-C_{12})$alkyl, N-piperidinyl$(C_1-C_{12})$ alkyl;

$R_4$, and $R_5$ are independently selected from hydrogen, halo, $(C_1-C_8)$alkyl, $(C_1-C_8)$alkoxy, cyano, halo $(C_1-C_{12})$alkyl, $(C_2-C_8)$alkenyl, $(C_3-C_{10})$alkynyl, aryl and aralkyl; and $R_6$ is $(C_1-C_{12})$ alkylenyl and $(C_2-C_{12})$alkenylenyl.

17 Claims, No Drawings

DIHYDROPYRIDAZINONES AND PYRIDAZINONES AND THEIR USE AS FUNGICIDES AND INSECTICIDES

This application claims the benefit of prior U.S. Provisional Application No. 60/028,336 filed Oct. 11, 1996.

This invention relates to dihydropyridazinones, pyridazinones and related compounds, compositions containing these compounds and methods for controlling fungi and insects by the use of a fungitoxic and insecticidal amount of these compounds.

U.S. Pat. No. 5,552,409 entitled "Dihydropyridazinones, Pyridazinones and Related Compounds and Their Use As Fungicides" discloses pyridazinone compounds as effective fungicides. These pyridazinones fail to possess a phenyl substituted ring substituted with a N-alkoxymethylcarbamate. The present inventions are novel compositions which have also been discovered to possess fungicidal and insecticidal properties.

The dihydropyridazinones and pyridazinones of the present invention have the Formula (I)

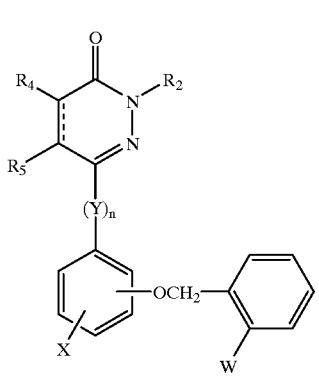

(I)

wherein W is

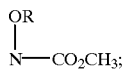

n is 0 or 1;

Y is O, S, $NR_1$, or $R_6$;

the ring bond containing $R_4$ and $R_5$ is a single or double bond;

X is independently selected from hydrogen, halo, $(C_1–C_4)$ alkyl, $(C_1–C_4)$alkoxy and —HC=CH—CH=CH— thereby forming a napthyl ring;

R is independently selected from $(C_1–C_{12})$alkyl and halo $(C_1–C_{12})$alkyl;

$R_1$ is independently selected from $(C_1–C_{12})$alkyl, $(C_2–C_8)$ alkenyl and aryl;

$R_2$ is independently selected from hydrogen, $(C_1–C_{12})$ alkyl, $(C_1–C_{12})$alkoxy, halo$(C_1–C_{12})$alkyl, halo $(C_1–C_{12})$alkoxy, hydroxy$(C_1–C_{12})$alkyl, $(C_1–C_{12})$ alkoxy$(C_1–C_{12})$alkyl, $(C_1–C_{12})$alkoxycarbonyl $(C_1–C_{12})$alkyl, $(C_2–C_8)$alkenyl, halo$(C_2–C_8)$alkenyl, $(C_3–C_{10})$alkynyl, halo$(C_3–C_{10})$alkynyl, $(C_3–C_7)$ cycloalkyl, $(C_3–C_7)$cycloalkyl$(C_1–C_4)$alkyl, epoxy $(C_1–C_{12})$alkyl, $PO(OR_1)_2(C_1–C_{12})$alkyl, $R_1S(O)_2$ $(C_1–C_{12})$alkyl, $(R_1)_3Si(C_1–C_{12})$alkyl, aryl, aryloxy $(C_1–C_{12})$alkyl, arylcarbonyl$(C_1–C_{12})$alkyl, aralkyl, arylalkenyl, heterocyclic, heterocyclic $(C_1–C_{12})$alkyl, N-morpholino$(C_1–C_{12})$alkyl and N-piperidinyl $(C_1–C_{12})$alkyl;

$R_4$ and $R_5$ are independently selected from hydrogen, halo, $(C_1–C_8)$alkyl, $(C_1–C_8)$alkoxy, cyano, halo $(C_1–C_{12})$alkyl, $(C_2–C_8)$alkenyl, $(C_3–C_{10})$alkynyl, aryl and aralkyl; and $R_6$ is $(C_1–C_{12})$ alkylenyl and $(C_2–C_{12})$alkenylenyl.

The aforementioned $(C_1–C_{12})$alkyl, $(C_1–C_{12})$alkoxy, $(C_2–C_8)$alkenyl, $(C_3–C_{10})$alkynyl and $(C_3–C_7)$cycloalkyl groups may be optionally substituted with up to three substituents selected from the group consisting of halogen, nitro, trihalomethyl and cyano.

The term alkyl includes both branched and straight chained alkyl groups from 1 to 12 carbon atoms. Typical alkyl groups are methyl, ethyl, n-propyl, isopropyl, n-butyl, sec-butyl, isobutyl,t-butyl, n-pentyl, isopentyl, n-hexyl, n-heptyl, isooctyl, nonyl, decyl, undecyl, dodecyl and the like. The term haloalkyl refers to an alkyl group further substituted with 1 to 3 halogens.

The term alkenyl refers to an ethylenically unsaturated hydrocarbon group, straight or branched, having a chain length of 2 to 12 carbon atoms and 1 or 2 ethylenic bonds. The term haloalkenyl refers to an alkenyl group substitued with 1 to 3 halogen atoms. The term alkynyl refers to an unsaturated hydrocarbon group, straight or branched, having a chain length of 2 to 12 carbon atoms and 1 or 2 acetylenic bonds.

The term alkylenyl refers to a bivalent alkyl group in which two free bonds can be on the same carbon or different carbons. The term alkenylenyl refers to a bivalent alkenyl group in which the two free bonds are on different carbons, an alkenyl group may also be substituted with 1 to 3 halo atoms.

The term cycloalkyl refers to a saturated ring system having 3 to 7 carbon atoms.

The term aryl includes phenyl or napthyl, which maybe substituted with up to three substituents selected from the group consisting of halogen, cyano, nitro, trihalomethyl, phenyl, phenoxy, $(C_1–C_4)$alkyl, $(C_1–C_4)$alkylthio, $(C_1–C_4)$ alkylsulfoxide $(C_1–C_6)$alkoxy and halo$(C_1–C_4)$alkyl.

Typical aryl substituents include but are not limited to 4-chlorophenyl, 4-fluoro-phenyl, 4-bromophenyl, 2-methoxyphenyl, 2-methylphenyl, 3-methyphenyl, 4-methyl-phenyl, 2,4-dibromophenyl, 3,5-difluorophenyl, 2,4,6-trichlorophenyl, 4-methoxyphenyl, 2-chloronapthyl, 2,4-dimethoxphenyl, 4-(trifluoromethyl)phenyl and 2-iodo-4-methylphenyl.

The term heterocyclic refers to a substituted or unsubstituted 5 or 6 membered unsaturated ring containing one, two or three heteroatoms, preferably one or two heteroatoms selected from oxygen, nitrogen and sulfur; or is a bicyclic unsaturated ring system containing up to 10 atoms including one heteratom selected from oxygen, nitrogen and sulfur.

The term aralkyl is used to describe a group wherein the the alkyl chain is from 1 to 10 carbon atoms and can be branched or straight chain, preferably a straight chain, with a terminal aryl portion, as defined above. Typical aralkyl moieties include but are not limited to benzyl, phenethyl, phenpropyl and phenbutyl moieties. The aralkyl moieties may be further substituted with from 1 to 5 substitiuents independently selected from the group consisting of halogen, halo$(C_1–C_4)$alkyl, $(C_1–C_4)$alkoxy and cyano.

Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4-dichlorobenzyl, 2,4-dibromobenzyl, 2-methylbenzyl, 3-methylbenzyl, and 4-methylbenzyl. Typical phenethyl moieties are 2-(2-chlorophenyl)ethyl, 2-(3-chlorophenyl)ethyl, 2-(4-chlorophenyl)ethyl, 2-(2-fluorophenyl)ethyl, 2-(3-fluorophenyl)ethyl, 2-(4-fluorophenyl)ethyl, 2-(2-methylphenyl)ethyl, 2-(3-methylphenyl)ethyl, 2-(4-methylphenyl)ethyl, 2-(4-trifluoromethylphenyl)ethyl, 2-(2-methoxyphenyl)ethyl, 2-(3-methoxyphenyl)ethyl, 2-(4-methoxyphenyl)ethyl, 2-(2,4-dichlorophenyl)ethyl, 2-(3,5-dimethoxyphenyl)ethyl. Typical phenpropyl moieties are 3-phenylpropyl, 3-(2-chlorophenyl)propyl, 3-(3-chlorophenyl)propyl, 3-(4-chlorophenyl)propyl, 3-(2,4-dichlorophenyl)propyl, 3-(2-fluorophenyl)propyl, 3-(3-fluorophenyl)propyl, 3-(4-fluorophenyl)propyl, 3-(2-methylphenyl) propyl, 3-(3-methylphenyl)propyl, 3-(4-methylphenyl)-ethyl, 3-(2-methoxyphenyl)propyl, 3-(3-methoxyphenyl)propyl, 3-(4-methoxyphenyl)propyl, 3-(4-trifluoromethylphenyl)propyl, 3-(2,4-dichlorophenyl)propyl and 3-(3,5-dimethoxyphenyl)propyl. Typical phenbutyl moities include are 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)butyl, 4-(2-methylphenyl)butyl, 4-(3-methylphenyl)butyl, 4-(4-methylphenyl)butyl, 4-(2,4-dichlorophenyl)butyl, 4-(2-methoxyphenyl)butyl, 4-(3-methoxyphenyl)butyl and 4-(4-methoxy-phenyl)butyl.

Halogen or halo is meant to include iodo, fluoro, bromo and chloro moieties.

A preferred embodiment of this invention are the compounds, enantiomorphs, salts and complexes of Formula (I) is when R is methyl, $R_4$ and $R_5$ are hydrogen and $R_2$ is $(C_1-C_{12})$alkyl, $(C_2-C_8)$alkenyl, phenyl or benzyl substituted with preferably two substituents independently selected from halo, trihalomethyl, cyano, $(C_1-C_4)$alkyl, $(C_1-C_4)$alkylthio, $(C_1-C_4)$alkoxy or phenyl, the bond containing $R_4$ and $R_5$ is a double bond and Y is a direct carbon bond, where n is 0, and where the $OCH_2$(2-W-aryl) is bonded at the meta position to Y.

A more preferred embodiment of this invention are the compounds, enantiomorphs, salts and complexes of Formula (I) is when $R_4$ and $R_5$ are hydrogen, $R_2$ is methyl, ethyl, allyl or n-propyl.

Typical compounds encompassed by the present invention of formulas II, III, and IV include those compounds presented in Tables 1, 2 and 3.

TABLE 1

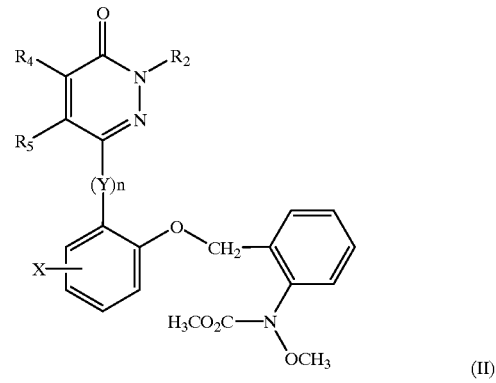

(II)

| Cmpd # | $R_2$ | $R_4$ | $R_5$ | X | Y | n |
|---|---|---|---|---|---|---|
| 1 | $CH_3$ | H | H | H | — | 0 |
| 2 | $CH_2CH_3$ | H | H | H | — | 0 |
| 3 | $CH(CH_3)_2$ | H | H | H | — | 0 |
| 4 | $CH_2CH(CH_3)_2$ | H | H | H | — | |
| 5 | $CH_2(CH_2)_2CH_3$ | H | H | H | — | 0 |
| 6 | $CH_2(CH_2)_3CH_3$ | H | H | H | — | 0 |
| 7 | $CH_2(CH_2)_4CH_3$ | H | H | H | — | 0 |
| 8 | Ar | H | H | H | — | 0 |
| 9 | $CH_2Ar$ | H | H | H | — | 0 |
| 10 | $CH_2Ar$(4Cl) | H | H | H | — | 0 |
| 11 | $CH_3CH_2Ar$ | H | H | H | — | 0 |
| 12 | $CH_3CH_2Ar$(4Cl) | H | H | H | — | 0 |
| 13 | $(CH_2)_3Ar$ | H | H | H | — | 0 |
| 14 | $(CH_2)_3Ar$(4Cl) | H | H | H | — | 0 |
| 15 | $CH_2CF_3$ | H | H | H | — | 0 |
| 16 | $CH_2CH_2F$ | H | H | H | — | 0 |
| 17 | $CH_2$cyclopropyl | H | H | H | — | 0 |
| 18 | $CH_2CH=CH_2$ | H | H | H | — | 0 |
| 19 | $CH_2CH_2CH=CH_2$ | H | H | H | — | 0 |
| 20 | $CH_2CCH$ | H | H | H | — | 0 |
| 21 | $CH_2CO_2CH_3$ | H | H | H | — | 0 |
| 22 | $CH_3CH_2CO_2CH_3$ | H | H | H | — | 0 |
| 23 | $CH_2$-(2-pyridinyl) | H | H | H | — | 0 |
| 24 | $CH_2$-(3-pyridinyl) | H | H | H | — | 0 |
| 25 | $CH_2$-(4-pyridinyl) | H | H | H | — | 0 |
| 26 | $CH_2$-1H-1,2,4-triazole | H | H | H | — | 0 |
| 27 | $(CH_2)_4Ar$ | H | H | H | — | 0 |

TABLE 2

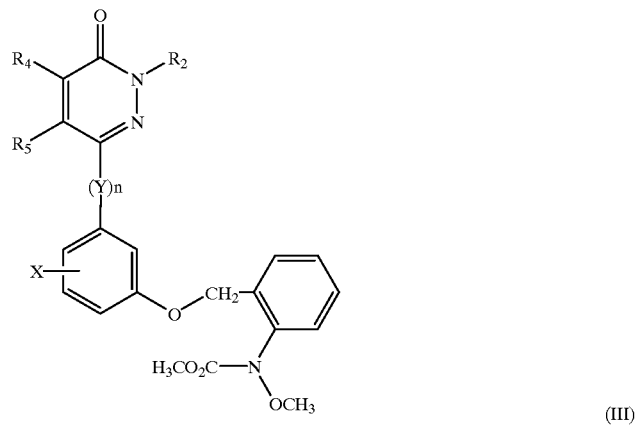

(III)

| Cmpd # | R$_2$ | R$_4$ | R$_5$ | X | Y | n |
|---|---|---|---|---|---|---|
| 28 | CH$_3$ | H | H | H | — | 0 |
| 29 | CH(CH$_3$)$_2$ | H | H | H | — | 0 |
| 30 | CH$_2$CH(CH$_3$)$_2$ | H | H | H | — | 0 |
| 31 | C(CH$_3$)$_3$ | H | H | H | — | 0 |
| 32 | CH$_2$(CH$_2$)$_3$CH$_3$ | H | H | H | — | 0 |
| 33 | C(CH$_3$)CH$_2$CH$_2$CH$_3$ | H | H | H | — | 0 |
| 34 | CH$_2$C(CH$_3$)$_3$ | H | H | H | — | 0 |
| 35 | CH$_2$CH$_2$OCH$_2$CH$_3$ | H | H | H | — | 0 |
| 36 | CH$_2$CH(CH$_3$)OH | H | H | H | — | 0 |
| 37 | CH$_2$CH$_2$OCOCH$_3$ | H | H | H | — | 0 |
| 38 | CH$_2$OCOAr | H | H | H | — | 0 |
| 39 | CH$_2$CH$_2$OCOAr | H | H | H | — | 0 |
| 40 | CH$_2$CH$_2$Br | H | H | H | — | 0 |
| 41 | (CH$_2$)$_2$Ar(4Cl) | H | H | H | — | 0 |
| 42 | (CH$_2$)$_3$Ar(4Cl) | H | H | H | — | 0 |
| 43 | (CH$_2$)$_4$Ar | H | H | H | — | 0 |
| 44 | (CH$_2$)$_2$OAr | H | H | H | — | 0 |
| 45 | CH$_2$C(Cl)=CH$_2$ | H | H | H | — | 0 |
| 46 | CH$_2$CCH | H | H | H | — | 0 |
| 47 | CH$_2$CH$_2$OAr | H | H | 3'-OMe | — | 0 |
| 48 | CH$_2$OCH$_2$Ar | H | H | H | — | 0 |
| 49 | CH$_2$CH$_2$OCH$_2$Ar | H | H | H | — | 0 |
| 50 | CH$_2$CH=CHAr | H | H | H | — | 0 |
| 51 | 2-pyridinyl | H | H | H | — | 0 |
| 52 | 4-pyridinyl | H | H | H | — | 0 |
| 53 | 2-pyrimidinyl | H | H | H | — | 0 |
| 54 | 4-pyrimidinyl | H | H | H | — | 0 |
| 55 | CH$_2$-(2-pyridinyl) | H | H | H | — | 0 |
| 56 | CH$_2$-(3-pyridinyl) | H | H | H | — | 0 |
| 57 | CH$_2$-pyrdzinyl | H | H | H | — | 0 |
| 58 | CH$_2$-(2-thienyl) | H | H | H | — | 0 |
| 59 | CH$_2$-(3-thienyl) | H | H | H | — | 0 |
| 60 | CH$_2$-(1-morpholinyl) | H | H | H | — | 0 |
| 61 | CH$_2$-(1-piperidinyl) | H | H | H | — | 0 |
| 62 | CH$_2$-(2-furyl) | H | H | H | — | 0 |
| 63 | CH$_2$-epoxide | H | H | H | — | 0 |
| 64 | CH$_2$—Si(CH$_3$)$_3$ | H | H | H | — | 0 |
| 65 | CH$_2$—Si(CH$_3$)$_2$-t-butyl | H | H | H | — | 0 |
| 66 | CH$_2$—Si(CH$_3$)$_2$Ar | H | H | H | — | 0 |
| 67 | CH$_2$—PO(OCH$_3$)$_2$ | H | H | H | — | 0 |
| 68 | CH$_2$—PO(OC$_2$H$_5$)$_2$ | H | H | H | — | 0 |
| 69 | CH$_2$OSO$_2$CH$_3$ | H | H | H | — | 0 |
| 70 | CH$_2$OSO$_2$Ar | H | H | H | — | 0 |
| 71 | CH$_2$-(4-CF$_3$-pyridin-2-yl) | H | H | H | — | 0 |
| 72 | CH$_2$-(1-napthyl) | H | H | H | — | 0 |
| 73 | CH$_2$-(2-napthyl) | H | H | H | — | 0 |
| 74 | CH$_2$—CO$_2$C$_2$H$_5$ | H | H | H | — | 0 |
| 75 | CH$_2$—CH=CH—CO$_2$CH$_3$ | H | H | H | — | 0 |
| 76 | CH$_2$CH$_2$CH$_2$CN | H | H | H | — | 0 |
| 77 | CH$_2$—CH=C(CH$_3$)$_2$ | H | H | H | — | 0 |
| 78 | CH$_2$—C(CH$_3$)=CHCH$_3$ | H | H | H | — | 0 |
| 79 | CH$_2$—C(CH$_3$)=C(CH$_3$)$_2$ | H | H | H | — | 0 |
| 80 | C$_2$H$_5$ | CH$_3$ | CH$_3$ | H | — | 0 |
| 81 | CH$_2$CH$_2$CH$_3$ | CH$_3$ | CH$_3$ | W | — | 0 |
| 82 | CH$_2$CF$_3$ | CH$_3$ | CH$_3$ | H | — | 0 |
| 83 | CH$_2$CH(CH$_3$)$_2$ | CH$_3$ | CH$_3$ | H | — | 0 |

TABLE 2-continued (III)

| Cmpd # | R$_2$ | R$_4$ | R$_5$ | X | Y | n |
|---|---|---|---|---|---|---|
| 84 | C(CH$_3$)$_3$ | CH$_3$ | CH$_3$ | H | — | 0 |
| 85 | CH$_2$(CH$_2$)$_3$CH$_3$ | CH$_3$ | CH$_3$ | H | — | 0 |
| 86 | CH(CH$_3$)(CH$_2$)$_2$CH$_3$ | CH$_3$ | CH$_3$ | H | — | 0 |
| 87 | (CH$_2$)$_2$CH(CH$_3$)$_2$ | CH$_3$ | CH$_3$ | H | — | 0 |
| 88 | CH$_2$C(CH$_3$)$_3$ | CH$_3$ | CH$_3$ | H | — | 0 |
| 89 | C$_2$H$_5$ | H | H | 3'Cl | — | 0 |
| 90 | CH$_2$CH$_2$CH$_3$ | H | H | 3'OCH$_3$ | — | 0 |
| 91 | CH(CH$_3$)$_2$ | H | H | 3'Cl | — | 0 |
| 92 | CH$_2$CH(CH$_3$)$_2$ | H | H | 3'OCH$_3$ | — | 0 |
| 93 | C(CH$_3$)$_3$ | H | H | 3'Cl | — | 0 |
| 94 | CH$_2$(CH$_2$)$_3$CH$_3$ | H | H | 3'OCH$_3$ | — | 0 |
| 95 | CH(CH$_3$)CH$_2$CH$_2$CH$_3$ | H | H | 3'Cl | — | 0 |
| 96 | (CH$_2$)$_2$CH(CH$_3$)$_2$ | H | H | 3'OCH$_3$ | — | o |
| 97 | CH$_2$C(CH$_3$)$_3$ | H | H | 3'Cl | — | 0 |
| 98 | CH$_2$CCH | H | H | 3'OCH$_3$ | — | 0 |
| 99 | CH$_3$ | H | H | H | O | 1 |
| 100 | CH$_2$CH$_3$ | H | H | H | O | 1 |
| 101 | CH$_2$CF$_3$ | H | H | H | O | 1 |
| 102 | CH$_2$(CH$_2$)$_3$CH$_3$ | H | H | H | O | 1 |
| 103 | CH(CH$_3$)CH$_2$CH$_2$CH$_3$ | H | H | H | O | 1 |
| 104 | (CH$_2$)$_2$CH(CH$_3$)$_2$ | H | H | H | O | 1 |
| 105 | CH$_2$C(CH$_3$)$_3$ | H | H | H | O | 1 |
| 106 | CH$_2$CH$_2$OH | H | H | H | O | 1 |
| 107 | CH$_2$(H(CH$_3$)OH | H | H | H | O | 1 |
| 108 | CH$_2$CH$_2$F | H | H | O | 1 | |
| 109 | CH$_2$CH$_2$Cl | H | H | H | O | 1 |
| 110 | CH$_2$CH$_2$Br | H | H | H | O | 1 |
| 111 | (CH$_2$)$_2$Ar | H | H | H | O | 1 |
| 112 | (CH$_2$)$_2$Ar(4Cl) | H | H | H | O | I |
| 113 | (CH$_2$)$_3$Ar | H | H | H | O | 1 |
| 114 | (CH$_2$)$_2$OAr | H | H | H | O | 1 |
| 115 | CH$_2$-(2-pyridinyl) | H | H | H | O | 1 |
| 116 | CH$_2$-(3-pyridinyl) | H | H | H | O | 1 |
| 117 | CH$_2$-pyrazinyl | H | H | H | O | 1 |
| 118 | CH$_2$-(2-thienyl) | H | H | H | O | 1 |
| 119 | CH$_2$-(3-thienyl) | H | H | H | O | 1 |
| 120 | CH$_2$-(1-morpholinyl) | H | H | H | O | 1 |
| 121 | CH$_2$-(1-piperidinyl) | H | H | H | O | 1 |
| 122 | CH$_2$-(3-pyrimidinyl) | H | H | H | O | 1 |
| 123 | CH$_2$C(Cl)=CH$_2$ | H | H | H | O | 1 |
| 124 | CH$_2$CCH | H | H | H | O | 1 |
| 125 | CH$_2$-cyclo-C$_5$H$_9$ | H | H | H | O | 1 |
| 126 | CH$_2$CH$_2$OCH$_2$Ar | H | H | H | O | 1 |
| 127 | CH$_2$CH=CHAr | H | H | H | O | 1 |
| 128 | CH$_2$-1H-1,2,4-triazole | H | H | H | O | 1 |
| 129 | CH$_2$-(3-pyridinyl) | H | H | H | O | 1 |
| 130 | CH$_2$-(1-morpholinyl) | H | H | H | O | 1 |
| 131 | CH$_3$ | H | H | H | O | 1 |
| 132 | CH$_2$CH$_3$ | H | H | H | S | 1 |
| 133 | CH$_2$CH$_2$CH$_3$ | H | H | H | S | 1 |
| 134 | CH$_3$ | H | H | H | N—CH$_3$ | 1 |
| 135 | CH$_2$CH$_3$ | H | H | H | N—CH$_3$ | 1 |
| 136 | CH$_3$ | H | H | H | CH$_2$ | 1 |
| 137 | CH$_2$CH$_3$ | H | H | H | CH$_2$ | 1 |
| 138 | CH$_2$CH$_2$F | H | H | H | CH$_2$ | 1 |
| 139 | CH$_2$CH=CH$_2$ | H | H | H | CH$_2$ | 1 |

TABLE 2-continued (III)

| Cmpd # | $R_2$ | $R_4$ | $R_5$ | X | Y | n |
|---|---|---|---|---|---|---|
| 140 | $CH_2$-1H-1,2,4-triazole | H | H | H | $CH_2$ | 1 |
| 141 | $CH_2$-(3-pyridinyl) | H | H | H | $CH_2$ | 1 |
| 142 | $CH_2$-(1-morpholinyl) | H | H | H | $CH_2$ | 1 |

TABLE 3

(IV)

| Cmpd # | $R_2$ | $R_4$ | $R_5$ | X | Y | n |
|---|---|---|---|---|---|---|
| 143 | $CH_3$ | H | H | H | — | 0 |
| 144 | $CH_2CH_3$ | H | H | H | — | 0 |
| 145 | $CH_2CH_2CH_3$ | H | H | H | — | 0 |
| 146 | $CH_2(CH_2)_2CH_3$ | H | H | H | — | 0 |
| 147 | $CH_2(CH_2)_3CH_3$ | H | H | H | — | 0 |
| 148 | $CH(CH_3)CH_2CH_2CH_3$ | H | H | H | — | 0 |
| 149 | $(CH_2)_2CH(CH_3)_2$ | H | H | H | — | 0 |
| 150 | $CH_2C(CH_3)_3$ | H | H | H | — | 0 |
| 151 | $CH_2CH_2=CH_2$ | H | H | H | — | 0 |
| 152 | $CH_2CH_2OH$ | H | H | H | — | 0 |
| 153 | $CH_2CH_2OCOCH_3$ | H | H | H | — | 0 |
| 154 | $CH_2CH(CH_3)OH$ | H | H | H | — | 0 |
| 155 | $CH_2CH_2F$ | H | H | H | — | 0 |
| 156 | $CH_2CH_2Cl$ | H | H | H | — | 0 |
| 157 | $CH_2CH_2Br$ | H | H | H | — | 0 |
| 158 | $(CH_2)_2Ar$ | H | H | H | — | 0 |
| 159 | $(CH_2)_2Ar(4Cl)$ | H | H | H | — | 0 |
| 160 | $(CH_2)_3Ar$ | H | H | H | O | 1 |
| 161 | $(CH_2)_2OAr$ | H | H | H | O | 1 |
| 162 | $CH_2$-(2-pyridinyl) | H | H | H | — | 0 |
| 163 | $CH_2$-(3-pyridinyl) | H | H | H | — | 0 |
| 164 | $CH_2$-(4-pyridinyl) | H | H | H | — | 0 |
| 165 | $CH_2$-(3-pyrimidinyl) | H | H | H | — | 0 |

As used in Tables 1, 2, and 3 Ar is understood to be phenyl.

The pyridazinones and dihydropyridazinones of the of the present invention may be prepared by conventional synthetic routes. For example, pyridazinones of Formula (I), when n is 0 as in Formula (V) are prepared by alkylation of the 6-(hydroxy)phenyl-2,4,5-trisubstituted-pyridazin-3-one (VI) as shown in scheme A when R is methyl:

Scheme A

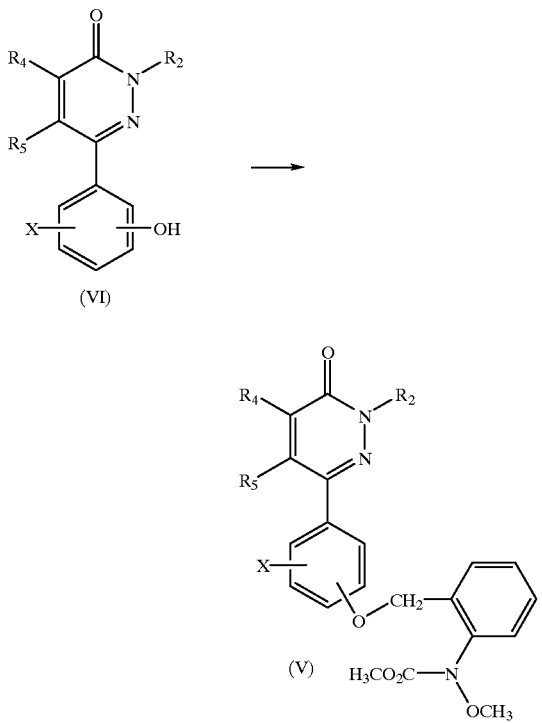

4,5,6-trisubstituted-3(2H)-pyridazinones (VI) and 4,5-dihydropyridazinones can be prepared as described in U.S. Pat. No. 5,552,409. Specifically 6-(hydroxyphenyl)-2-substituted-pyridazin-3-ones (VI, where $R_4=R_5=H$) are prepared as shown in Scheme B.

Scheme B

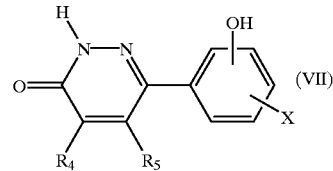

Alternatively, hydroxyacetophenones and glyoxalic acid can be treated with hydrazine to afford the 6-(hydroxyphenyl)-3(2H)-pyridazinone (VII) as shown in Scheme C. 2-, 3- or 4-hydroxysubstituted-acetophenones can be utilized in the condensations described in schemes B and C which provide the isomeric 6-(hydroxyphenyl) pyridazinones (VI and VII).

Scheme C

The pyridazinone (VII) is alkylated with commercially available $R_2$-L, where $R_2$ is as previously defined and L is halogen or another leaving group such a methanesulfonate (mesylate) or toluenesulfonate (tosylate), under basic conditions such as NaH in dimethylformamide (DMF), potassium hydroxide in DMSO or potassium carbonate in DMF or acetone, and provides a mixture of N and O alkylated products as shown in Scheme D. The nitrogen monoalkylated product (VI) can be separated by conventional chromatographic techniques and treated with 2-W-benzylbromide to provide (V) or a mixture of (VI) and (VIII) can be alkylated with the benzyl bromide, in situ (without isolation of (VI) or (VIII)), after which (V) is separated by chromatography from unreacted (VIII).

Scheme D

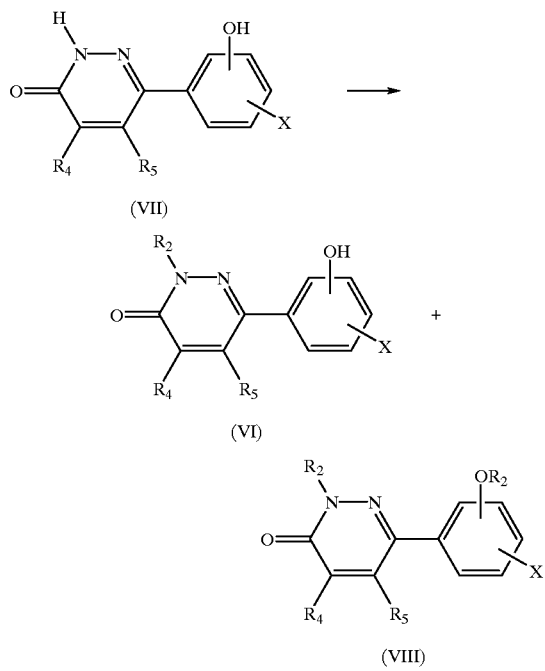

Alternatively, the pyridazinone (VII) is dialkylated in the presence of 2 equivalents of $R_2X$ under basic conditions such as NaH in DMF, potassium hydroxide in dimethylsulfoxide (DMSO) or potassium carbonate in DMF or acetone, and provides the O,N-dialkylated product VIII as shown in Scheme E. The dialkylated product (VIII) is treated with either HBr, BBr$_3$ or HI at elevated temperatures, preferably at 90 to 100° C., and the O-alkyl group is selectively cleaved to provide the N-substituted intermediate (VI). The monoalkylated product (VI) is treated with 2-W-benzylbromide to provide (V).

Scheme E

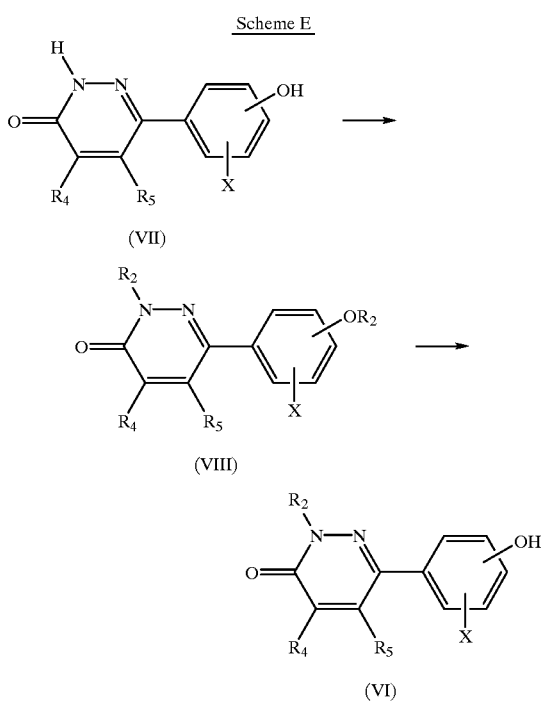

The dihydropyridazinone (IX) is prepared by the reduction of the N-substituted intermediate (VI). Reduction with Zn in HOAc, at room temperrature provides the dihydropyridazinone (IX), as shown in Scheme F, which is treated with 2-W-benzylbromide to provide (X).

Scheme F

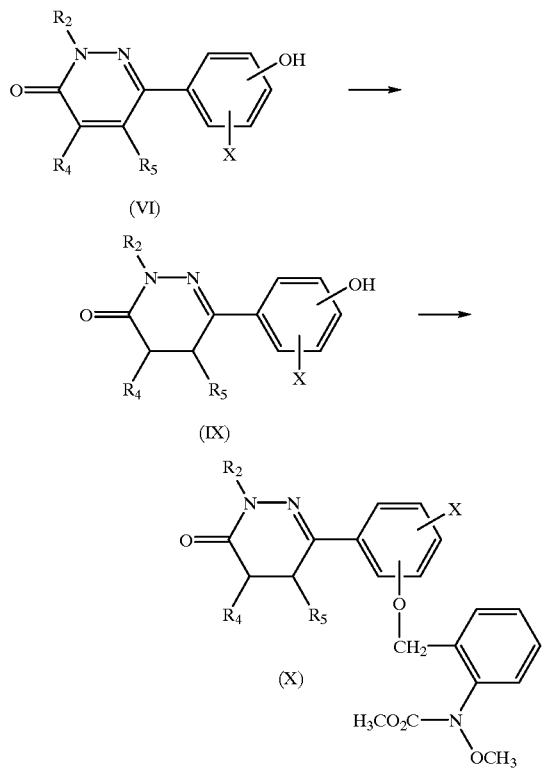

The 2-W-benzylbromide, methyl N-(2-bromomethylphenyl)-N-alkoxycarbamate, is prepared as described in both EP619301 and EP704430 in a 4 step sequence as shown in scheme G. As described in the aforementioned European patent applications o-nitrotoluene is reacted with ammonium chloride in the presence of zinc to provide N-2-methylhydroxylamine (XI) as described in *Organic Synthesis Collective Volume* III, p.668. The hydroxylamine is acylated with methyl chloroformate to provide the methyl N-hydroxycarbamate (XII) which is alkylated, for example with dimethylsulfate (R is methyl), to provide (XIII) which is brominated under standard conditions such as N-bromosuccinimide in carbontetrachloride in the presence of a catalyst such as benzoyl peroxide to afford the intermediate benzylbromide (XIV).

Scheme G

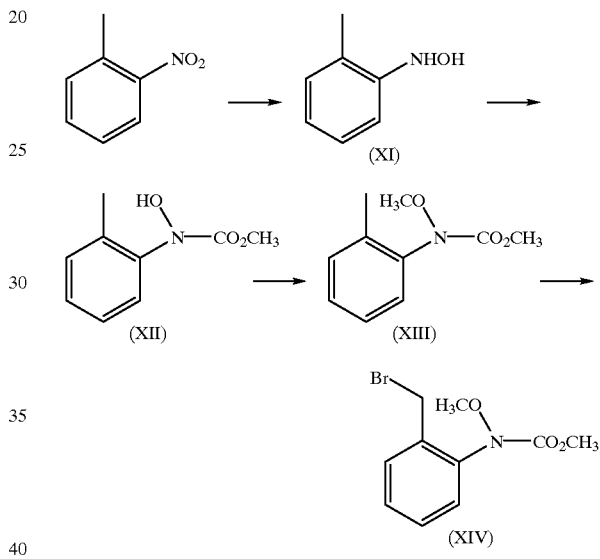

Compounds of Formula (I) where n=1, and more specifically, Y is oxygen are prepared as is shown in Scheme H.

Scheme H

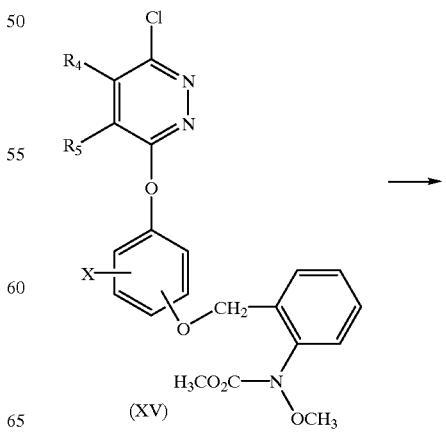

-continued

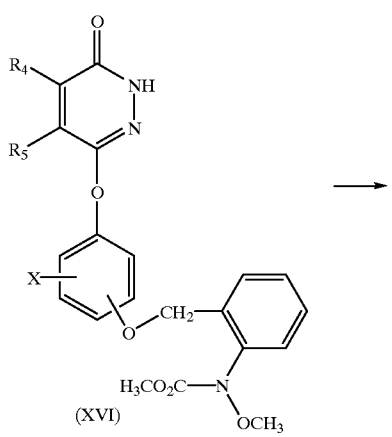
(XVI)

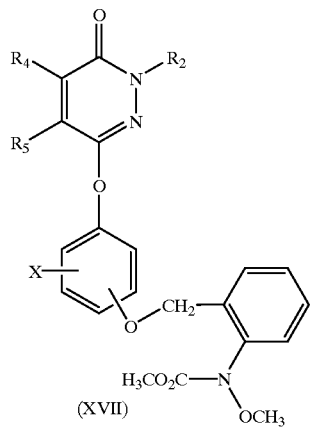
(XVII)

The alkylation of (XVI) with $R_2$-L proceeds under basic conditions, similiar to those described for (VI), to provide (XVII). The 6-((2'-(W)benzyloxy)phenoxy)-4,5-disubstituted-3(2H)-pyridazinone (XVI) is prepared by acidic hydrolysis of the 6-((2'-(W)benzyloxy)phenoxy))-4,5-disubstituted-3-chloropyridazine (XV) which is prepared by alkylation of phenolic intermediate (XVIII), as shown in Scheme I. The 6-(hydroxyphenoxy)-4,5-disubstituted-3-chloropyridazine (XVIII) is prepared by the reaction of dichloropyridazine with dihydroxybenzene, such as resorcinol and catechol as shown in Scheme I.

Scheme I

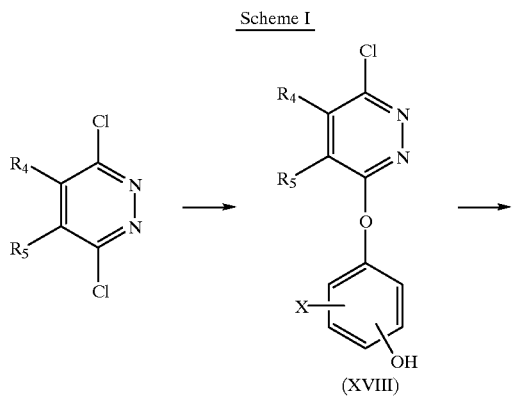
(XVIII)

-continued

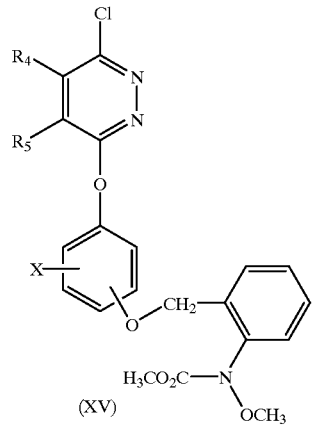
(XV)

Compounds of Formula (I) wherein Y is S or N—$R_6$ can be prepared in an analogous sequence as described in Schemes H and I. When Y is S, substituted mercaptophenols are utilized, likewise when Y is N—$R_6$, substituted aminophenols are utilized.

Compounds of Formula (V), (X) and (XVII) can also be prepared by alkylation of (VI), (IX) or (XVI) with 2-nitrobenzylbromide as shown in scheme J. The resulting nitrobenzyloxy intermediates (XX) are reduced, acylated and alkylated in a similiar manner as is described in Scheme G for o-nitrotoluene.

Scheme J

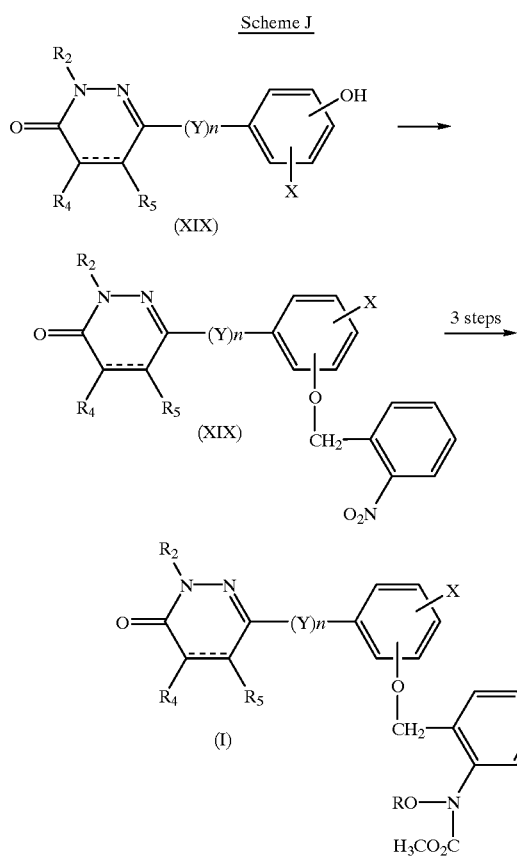

The following examples in Table 4 are provided to illustrate the present invention.

TABLE 4

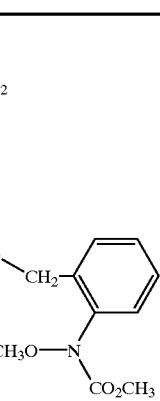

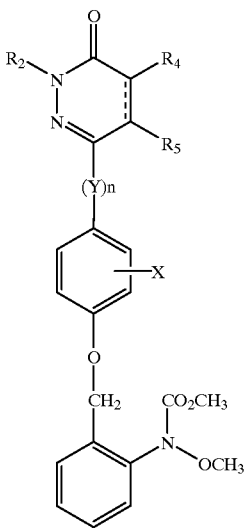

| Cmpd # | FORMULA | R₂ | R₄ | R₅ | X | R4-R5 ring bond | Y | n |
|---|---|---|---|---|---|---|---|---|
| 166 | III | ethyl | H | H | H | C=C | — | 0 |
| 167 | III | n-propyl | H | H | H | C=C | — | 0 |
| 168 | III | n-propyl | H | H | H | C—C | — | 0 |

The compounds of this invention can be made according to the the following procedures:

EXAMPLE 1

N-methoxy-N-methyl-N-[2-(3-(2'-(n-propyl)pyridazin-3'-on-6'-yl)phenyl)oxymethyl-phenyl]carbamate. (Table 4; Compound 167)

To a 250 ml round bottom flask, stirring under a nitrogen atomsphere, was charged with 1.5 g (1.0 equivalents (eq.), 6.6 mmoles) of 6-(3-hydroxyphenyl)-2-(n-propyl)-3(2H)-pyridazinone (prepared in an analogous manner as in Example 5 using n-propyl bromide) and 20 milliliters(ml) of dimethylformamide (DMF). To this solution was added 0.74 g (2.0 eq., 13.2 mmoles) of powdered 87% potassium hydroxide (KOH) and was stirred for 15 minutes (min.). To the reaction mixture was added 2.6 g of methyl N-(2-bromomethylphenyl)-N-methoxycarbamate (70% pure, 1.0 eq., 6.6 mmoles) in 10 ml of DMF. The reaction was stirred at ambient temperature and monitored by gas liquid chromatography (glc). After 45 min. the reaction was complete and quenched by pouring into 75 ml of water and 75 mls of EtOAc. To this was added 75 ml EtOAc, 50 ml ether and 50 ml of water. The organic phase was separated and washed with 150 ml of water, 150 ml of 10%NaOH, 3×150 ml of water and dried over anhydrous magnesium sulfate (MgSO₄) and filtered. The filtrate was concentrated by evaporation under reduced pressure to afford 3.7 g of crude product as an oil which was purified by flash chromatography with 75% EtOAc: 25% hexanes. The pure fractions were combined to yield 2.0 g of N-methoxy-N-methyl-N-[2-(3-(2'-(n-propyl)pyridazin-3'-on-6'-yl)phenyl)oxymethyl-phenyl]carbamate as a light orange oil(71.6% yield).

NMR(¹H₁, 300 MHz, CDCL₃): 1.0(t,3H), 1.9(q,2H), 3.76 (s,3H), 2.81(s,3H), 4.20(t,2H), 5.18(s,2H), 7.0–7.65(m, 10H).

EXAMPLE 2

N-methoxy-N-methyl-N-[2-(3-(2'-(n-propyl)-4,5-dihydropyridazin-3'-on-6'-yl)phenyl)oxymethyl-phenyl]carbamate. (Table 4; Compound 168)

To a 250 ml round bottom flask, stirring under a nitrogen atomsphere, was charged with 1.2 g (1.0 eq., 5.2 mmoles) of 6-(3-hydroxyphenyl)-2-(n-propyl)-3(2H)-4,5-dihydropyridazinone and 20 mls of dimethylformamide (DMF). To this solution was added 0.58 g (2.0 eq., 10.4 mmoles) of powdered 87% KOH and was stirred for 15 min. To the reaction mixture was added 2.05 g of methyl N-(2-bromomethylphenyl)-N-methoxycarbamate (70% pure, 1.0 eq., 5.2 mmoles) in 10 ml of DMF. The reaction was stirred at ambient temperature and monitored by glc. After 2 hours (hr.) the reaction was complete and quenched by pouring into 75 ml of water and 75 ml of EtOAc. To this was added 75 ml EtOAC, 50 ml ether and 50 ml of water. The organic phase was separated and washed with 150 ml of water, 150 ml of 10%NaOH, 3×150 ml of water and dried over anhydrous MgSO₄ and filtered. The filtrate was concentrated by evaporation under reduced pressure to afford 2.3 g of crude product as an oil which was purified by flash chromatography with 75% EtOAc: 25% hexanes. The pure fractions were combined to yield 1.3 g of N-methoxy-N-methyl-N-[2-(3-(2'-(n-propyl)pyridazin-3'-on-6'-yl)phenyl)oxymethyl-phenyl]carbamate as a light orange oil (58.8% yield).

NMR (¹H₁, 300 MHz, CDCL₃): 0.93(t,3H), 1.71(q,2H), 2.57(m,2H), 2.91(s,3H), 3.7–3.9(m, 8H), 5.1(s,2H), 6.95–7.6(m, 8H).

EXAMPLE 3

Preparation 6-(3-hydroxyphenyl)-2-(n-propyl)-3(2H)-4,5-dihydropyridazinone (Used to prepare the compound of Example 2.)

To a 500 ml 3 neck RBF, stirring under a nitrogen atmosphere was charged 12.0 g (52.0 mmoles) 6-(3-n-hydroxyphenyl)-2-(n-propyl)-3(2H)-pyridazinone, (prepared in an analogous manner as in Example 5 using n-propyl bromide), 5.1 g of zinc (1.5 eq., 78 mmoles) and 50 ml of glacial acetic acid. The reaction exothermed initially to 28° C. and was than stirred at ambient while monitoring by glc. After 2 hr., 3.3 g of zinc was added (50.0 mmoles) and the reaction was stirred at ambient temperature for an additional 3 hr. after which the reaction was complete by glc. The reaction was quenched by the addition of 400 ml of EtOAc to the reaction mixture. The mixture was vacuum filtered through a bed of celite and the solvent rtemoved on the rotovap. To the residue was added 500 ml of methylene chloride and washed with 4×400 ml of water, dried over anhydrous $MgSO_4$, and filtered. The filtrate was concentrated by evaporation under reduced pressure to afford 8.7 g of 6-(3-hydroxyphenyl)-2-(n-propyl)-3(2H)-4,5-dihydropyridazinone as tan solid (62.6% yield) which was used to prepare the compound of Example 2.

EXAMPLE 4

N-methoxy-N-methyl-N-[2-(3-(2'-ethylpyridazin-3'-on-6'-yl)phenyl)oxymethylphenyl]carbamate. (Table 4; Compound 166)

To a 250 ml round bottom flask, stirring under a nitrogen atomsphere, was charged 1.2 g (1.0 eq., 5.5 mmoles) of 6-(3-hydroxyphenyl)-2-ethyl-3(2H)-pyridazinone in 20 ml of DMF followed by 0.34 g of 87% KOH powdered pellets (1.10 eq., 6.1 mmoles). The reaction was stirred for 10min. after which 1.9 g of methyl N-(2-bromomethylphenyl)N-methoxycarbamate (70% pure, 0.9 eq., 4.8 mmoles) in 10 ml of DMF. The reaction was stirred at ambient temperature and monitored by GLC and after 3 hr. an 0.25 g of KOH (4.4 mmoles) and 0.4 g (1.0 mmole) of methyl N-(2-bromomethylphenyl)-N-methoxycarbamate were added. After 3 hr. the reaction was complete and quenched by pouring into 75 mls of water and 75 ml of EtOAc. To this was added 75 ml EtOAc, 75 ml ether and 75 ml of water. The organic phase was separated and washed with 2×150 ml of water, 150 ml of 10%NaOH, 3×150 ml of water and dried over anhydrous magnesium sulfate, and filtered. The filtrate was concentrated by evaporation under reduced pressure to afford 3.0 g of crude product as an oil which was purified by flash chromatography with 75% EtOAc: 25% hexanes. The pure fractions were combined to yield 1.9 g of N-methoxy-N-methyl-N-[2-(3-(2'-ethylpyridazin-3'-on-6'-yl)phenyl)oxymethyl-phenyl]carbamate as a light orange gummy resin (77.2% yield).

NMR ($^1H_1$, 300 MHz): 1.44(t,3H), 3.7(s, 3H), 3.8(s,3H) 4.3(q,2H), 5.2(s,2H), 6.95–7.7(m, 10H).

EXAMPLE 5

Preparation of 6-(3-hydroxyphenyl)-2-ethyl-3(2H)-pyridazinone (Used to prepare the compound of Example 4) via Scheme E.

Preparation of 6-(3-hydroxyphenyl)-3(2H)-pyridazinone

A 500 ml round bottom flask was equipped with a magnetic stirrer, thermometer, addition funnel, and pH electrode and was charged with 18.4 g (0.2 moles) of glyoxylic acid monohydrate and 75 ml of water. The solution was cooled to 10° C. and 20% aqueous potassium hydroxide was added raise the to pH to 8. A partial solution of 3'-hydroxyacetophenone (27.2 g, 0.2 moles) in KOH solution (20 g, 0.36 moles) was added all at once to the cold sodium glyoxylate solution and the reaction was stirred at room temperature for 2 hours. The dark brown solution was then re-cooled to 10° C., and acetic acid was added to pH 8. The contents were transferred to a separatory funnel, and the aqueous solution was extracted with 4×100 ml of methylene chloride to remove any unreacted 3'-hydroxyacetophenone. The aqueous fraction was again transferred to the reaction flask, cooled to 10° C. and further treated with acetic acid to pH 4.5, then concentrated ammonium hydroxide was added to pH 8. The solution was then heated under reflux with hydrazine monohydrate (10 ml, 0.2 moles) for 2 hours, then cooled to afford a yellow solid which was collected by vacuum filtration, and washed with water. The product was dried overnight under vacuum at 40° C., to yield 25.2 g of 6-(3-hydroxyphenyl)-3(2H)-pyridazinone (90.6% yield).

NMR (200 MHz, $d_6$-DMSO): 6.9(m,1H), 7.0(d,1H), 7.4 (m,3H), 8.0(d,1H), 9.8(br s,1H), and 13.2 (br s,1H).

Preparation of 6-(3-ethoxyphenyl)-2-ethyl-3(2H)-pyridazinone

To a 2 liter 4-neck round bottom flask, stirring under a nitrogen atomsphere, was charged 50.0 g (1.0 eq., 0.266 moles) of 6-(3-hydroxyphenyl)-3(2H)-pyridazinone in 500 ml of ethanol followed by 73.4 g of potassium carbonate (2.0 eq., 0.53 moles) and 58.0 g of ethyl bromide (2.0 eq., 0.53 moles) in 50 ml of ethanol. The reaction was stirred at reflux, 70° C.–72° C. for 6 hr. with monitoring by glc. After 6 hr. 5.8 g of ethylbromide was added (0.2 eq., 53 mmoles) and after stirring for an addtional 15 hr. at reflux glc indicated all the starting pyridazinone was consumed. The reaction was worked up by vacuum filtering the mixture while still warm and washing the solid with 2×150 ml of ethanol. The filtrate was concentrated by evaporation under reduced pressure to afford 67.3 g of 6-(3-ethoxyphenyl)-2-ethyl-3(2H)-pyridazinone as a brown oil which solidified.

NMR (200 MHz): 1.4(t, 6H); 4.1(q,2H); 4.2(q,2H); 6.9 (m,1H); 7.0(d,1H); 7.4(m,3H); 7.7(d,1H).

Preparation of 6-(3-hydroxyphenyl)-2-ethyl-3(2H)-pyridazinone

To a 2 liter 3-neck round bottom flask, stirring under a nitrogen atomsphere, was charged 64.9 g (1.0 eq., 0.266 moles) of 6-(3-ethoxyphenyl)-2-ethyl-3(2H)-pyridazinone followed by 250 ml of 48% HBr. The reaction was stirred at 90° C.–95° C. with monitoring by glc. After 7 hr. an additional 100 ml of 48%HBr was added and after an additional 10 hr. 100 ml of 48%HBr was added. After 33 hr. of stirring at 90° C.–95° C. the reaction was cooled to room temperature and quenched by pouring into 500 ml of ice water. An oil formed initially which on standing solidified. The solid was broken into small pieces and vacuum filtered, washed with 3×200 ml water and dried in a vacuum oven at ambient temperature and afforded 47.0 g of 6-(3-hydroxyphenyl)-2-ethyl-3(2H)-pyridazinone as a brown red solid. (81.9% yield).

NMR (200 MHz): 1.3(t,3H); 4.1(q,2H); 6.8(m,1H), 7.0 (d,1H); 7.3(m,3H); 8.0(d,1H)

EXAMPLE 6

Preparation of Methyl N-(2-bromomethylphenyl)-N-methoxycarbamate (used to prepare the compounds of Example 1, 2 and 3).

Preparation of N-2-methylphenylhydroxylamine

To a 1-L 3-neck round bottom flask was charged 28.6 g (1.0 eq., 0.21 moles) o-nitrotoluene in 200 ml ethyl alcohol and 28.7 g (2.1 eq, 0.44 moles) zinc powder neat. The reaction solution was heated to 45° C. and 13.5 g (1.2 eq., 0.25 moles) ammonium chloride in 120 ml water was added with an addition funnel controlling the exotherm in 50° C.–55° C. range with an ice-bath. The reaction was monitored by glc analysis and after 30 min. an additional 7.2 g (0.11 mole) zinc was added neat followed by 3.3 g (0.06 moles) ammonium chloride in 10 ml water.

The reaction was worked up after 45 min. by vacuum filtering the reaction mixture through celite, washing the wet cake with 50 ml ethyl alcohol and removing the solvent at 30° C. on the rotary evaporator to give orange oil. To the oil was added 300 ml ether and 200 ml water. The organic phase was separated and washed with 3×200 ml water using NaCl to break up the emulsion, dried over MgSO4-anhyd., and the ether was removed at 30° C. on the rotary evaporator to give 16.1 g product as an orange oil (62.3% yield) which was used directly in the next step.

Preparation of Methyl N-hydroxy-N-2-methylphenylcarbamate

To a 250 ml 3-neck RBF, stirring under nitrogen atmosphere, was charged 16.1 g (1.0 eq., 0.13 moles) N-2-methylphenylhydroxyamine in 40 ml methylene chloride and 16.8 g (1.5 eq., 0.20 moles) sodium bicarbonate neat. With a pipet added 13.1 g (1.05 eq, 0.37 moles) methyl chloroformate neat to the mixture at −5° C. to +5° C. The reaction mixture was stirred at 0° C. for 30 min. following the addition and the reaction was monitored by GC.

After 45 minutes the reaction was quenched by the addition of 100 ml methylene chloride and 100 ml water while cooling in an ice-bath. The reaction was worked up with an additional 100 ml of methylene chloride and water. The organic phase was separated, washed with 3×200 ml water, and the solvent removed at 30° C. on the rotary evaporator to give 21.3 g of the crude product as an orange gummy solid. Triturated with 40 ml hexanes and after crushing with a mortar and pestle the resulting solid was washed with 3×20 ml hexanes to give 15.35 g product as an off-white solid (65.3% yield).

NMR (H, 300 mhz): 2.31(s, 3H), 3.76 (s, 3H), 7.25–7.26 (m, 4H), and 7.78–7.81(br,1H)

Preparation of Methyl N-methoxy-N-2-methyl phenylcarbamate

To a 250 ml 3-neck RBF, stirring under nitrogen atmosphere, was charged 15.25 g (1.0 eq., 84.25 mmoles) methyl N-hydroxy-N-2-methyl phenylcarbamate in 30 ml methylene chloride and 17.4 g (1.5 eq., 0.126 moles) potassium carbonate neat causing a solid cake to form almost immediately. To the reaction mixture was added 150 ml more methylene chloride and the large cake was broken up into lumps with a spatula. To the reaction mixture was added 12.74 g (1.2 eq, 0.101 moles) dimethyl sulfate neat and the mixture was heated at 40° C. TLC was used to monitor the reaction after 1 hour and 3 hours and after 1 hr. 1.2 g(9.5 mmole) of dimethyl sulfate neat was added. The reaction mixture was quenched by pouring the reaction into 250 ml water after 3 hr.

The reaction was worked up up by the addition of 150 methylene chloride to the quenched reaction and partitioned the organic phase, washed with 3 by 250 ml water, dried over magnesium sulfate anhyrous. The solvent was removed at 45° C. on the rotary evaporator to give 20.8 g crude of product as light brown oil which contained dimethyl sulfate. 1.5 g of the crude product was washed with 10% ammonium hydroxide which removed the dimethyl sulfate and gave 0.9 g product. The remaining 19.3 g crude product containing the dimethyl sulfate was taken up in 250 ml ether, washed with 3×200 ml 10% ammonium hydroxide, with 3×200 ml water, dried over magnesium sulfate-anhyd. The solvent was removed at 45° C. on the rotary evaporator to give 12.4 g plus 0.9 g for a total of 13.3 g of methyl N-methoxy-N-2-methyl phenylcarbamate as a brown/orange oil (81.1% yield).

NMR (H, 300 MHz): 2.29(s, 3H), 3.73(s,3H), 3.78(s, 3H), 7.26(m, 4H)

Methyl N-2-bromomethylphenyl-N-methoxycarbamate

To a 500 ml 3-neck RBF under $N_2$ atmosphere was charged 12.0 g (1.0 eq, 61.5 mm) methyl N-methoxy-N-2-methyl phenylcarbamate in 70 ml $CCl_4$, 12.0 g (1.1 eq, 67.7 mmoles) N-bromosuccinimide (NBS) neat, 36 milligrams (mg.) of 2,2-azobis (2-methylpropionitrile) (AIBN), and heated at 77° C. reflux with a high intensity lamp for 10 h. During this time period an additional 300 mg. of AIBN and an additonal 3 g NBS was added.

The reaction mixture was worked up by vacuum filtration, washing the filtrate with 200 ml 2.5% sodium bisulfite, 200 ml 2.5% sodium bicarbonate, 2×200 ml water and drying with magnesium sulfate anhyd. The solvent was removed at 40° C. with the rotary evaporator to give 16.0 g of product as an orange oil (71% purity, 68.0% yield).

NMR (H, 300 MHz): 3.79(s, 3H), 3.80(s,3H), 4.5(s, 2H), 7.2–7.4(m, 4H)

EXAMPLE 7

Numerous compounds of this invention were tested for fungicidal activity in vivo against the diseases described below. The compounds were dissolved in a 2:1:1 mixture of water, acetone and methanol (by volume), sprayed onto the plants, allowed to dry (one to two hours) and then the plants were inoculated with the fungus. Each test utilized control plants which were sprayed with the water, acetone and methanol mixture and inoculated with the fungus. The remainder of the technique of each of the tests is given below and the results for various compounds described herein by the Example number in Table 4 against the various fungi at a dose of 300 grams per hectare. The results are reported as percent disease control, compared to the control wherein) one hundred was rated as total disease control and zero was no disease control. The application of the fungi to the test plants was as follows:

Wheat Leaf Rust (WLR)

*Puccinia recondita* (f. sp. tritici) was cultured on 7 day old wheat (cultivar Fielder) over a 14 day period in the greenhouse. Spores were collected from the leaves by settling on aluminum foil. The spores were cleaned by sieving through a 250 micron opening screen and stored or used fresh. Storage employed sealed bags in an Ultralow freezer. A spore suspension was prepared from dry uredia by adding 20 mg (9.5 million spores) per mL of Soltrol oil. The suspension was dispensed into gelatin capsules (0.7 mL capacity) which attach to the oil atomizers. One capsule is used per flat of twenty of the 2 inch square pots of 7 day old Fielder wheat. After waiting for at least 15 minutes for the oil to evaporate from the wheat leaves, the plants were placed in a dark mist chamber (18–20° C. and 100% relative humidity) for 24 hours. The plants were then put in the greenhouse for the latent period and scored after 10 days for disease levels. For protective tests the plants are inoculated one day after spraying the plants with the fungicide compounds.

Cucumber Downy Mildew (CDM)

*Pseudoperonospora cubensis* was maintained on leaves of live Bush Champion cucumber plants in a constant temperature room of 18 to 22° C. in humid air with moderate light intensity for 7 to 8 days. A water suspension of the spores from infested leaves was obtained and the spore concentration was adjusted to about $1 \times 10^5$ per ml of water. Bush Champion cucumber seedlings were inoculated by spraying the underside of leaves with a DeVilbiss atomizer until small drops were observed on the leaves. The innoculated plants were incubated in a mist chamber for 24 hours at about 70° F. and subsequently incubated for 6 to 7 days in a controlled temperature room under mist at 65 to 75° F. Seven days after inoculation the percent disease control was determined.

Grape Downy Mildew (GDM)

*Plasmopara uticola* was maintained on leaves of live grape plants, cv. Delaware, in the controlled temperature chamber at 20° C. in humid air with moderate light intensity for 7 to 8 days. A water suspension of the spores from infested leaves was obtained and the spore concentration was adjusted to about $3 \times 10^5$ per ml of water. Delaware grape plants were inoculated by spraying the underside of leaves with a De Vilbiss atomizer until small drops were observed on the leaves. The inoculated plants were incubated in a mist chamber for 24 hours at 20° C. Disease control values were recorded as percent control seven days after inoculation.

When tested against cucumber downy mildew at a dose of 300 grams per hectare, Examples 166, 167 and 168 exhibited 90% or better control. At 300 grams per hectare Examples 166, 167 and 168 exhibited 95 or better control against wheat leaf rust. Also at 300 grams/hectare, Examples 166, 167, and 168 provided 95% or better control against grape downy mildew.

The dihydropyridazinones and pyridazinones and the enantiomorphs, acid addition salts and metal salt complexes thereof are useful as agricultural fungicides and, as such, can be applied to various loci such as the seed, the soil or the foliage.

The dihydropyridazinones and pyridazinones, and the enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per hundred kilograms of seed. As a soil fungicide the chemical can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare.

In as much as the dihydropyridazinones and pyridazinones, and the enantio-morphs, salts and complexes thereof, display fungicidal activity, these compounds can be combined with other known fungicides to provide broad spectrum activity. Suitable fungicides include, but are limited to, those compounds listed in U.S. Pat. No. 5,252,594 (see in particular columns 14 and 15).

The dihydropyridazinones and pyridazinones, and the enantiomorphs, acid addition salts and metal salt complexes thereof can be advantageously employed in various ways. Since these compounds possess broad spectrum fungicidal activity, they can be employed in the storage of cereal grain. These complexes can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast.

EXAMPLE 8

Numerous compounds of this invention were tested for insecticidal activity in vivo against the insects described below. The following test method was used to evaluate compounds of the present invention for insectidal activity. The compound to be evaluated was dissolved in an appropriate solvent, usually a mix of acetone, methanol and water, and sprayed over three excised leaf disks using a flat fan nozzle. After spraying, the leaf disks were allowed to dry. Two disks were infested with the leaf chewing insects (southern armyworm and Mexican bean beetle) and the third leaf disk was already infested with the two-spotted spider mite prior to spraying. The tested insect species were:

| AW | southern armyworm | *Spodoptera eridamia* |
|---|---|---|
| BB | Mexican bean beetle | *Epilachna varivestis* |
| MTA | two-spotted spider mite | *Teranychus uricate* |

Observations as percent control were made by visual inspection 24–48 hours after spraying.

When tested against southern army worm at 600 grams/ hectare Examples 167 and 168 provided 75% or better control. When tested against Mexican bean beetle at 300 grams/hectare Examples 166, 167 and 168 provided 50% or better control.

The compositions and compounds of this invention can be applied directly to the locus to be protected, as for example, the area around or upon economic plants infected with insects or to plants on which infestation is to be prevented. Examples of injurious insects belong to the orders Lepidoptera, Coleoptera, Diptera, Thysanoptera, Hymenoptera, Heteroptera, Homoptera, Orthoptera, and Acarina. The compounds and compositions may be used either as contact or systemic pesticides. The compounds of the invention are applied to the insect's habitat at a rate of 0.0005 to 10 kilograms per hectare, preferably 0.05 to 5 and most preferably from 0.1 to 1 kilogram per hectare.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as "systemic" application. Alternatively, the active compound may be applied to the soil and contacted therein with the insects and other pests to be controlled. This means of application is referred to as "soil" application. In another alternative, the active compound may be foliarly applied to the plants to be freed from insects and other pests which feed on the foliage.

Compositions and formulations according to the present invention may also include known pesticidal compounds.

This expands the spectrum of activity of the preparation and may give rise to synergism. Suitable insecticides known in the art inlcude those listed in U.S. Pat. No. 5,075,471, see in particular columns 14 and 15.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier is meant any substance which can be used to dissolve, disperse of diffuse the active ingredient in the composition without impairing the active ingredients effectiveness and which by itself has no significant detrimental effect on the soil, equipment, desirable plants, or agronomic enviornment. If desired, adjuvants such as surfactants, stabilizers, antifoam agents and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instantinvention.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art, and a discussion of adjuvants can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001–99% by weight. For compositions suitable for storage or transportation, the amount of active ingredient is preferably between about 0.5–90% by weight, and more preferably between about 1–75% by weight of the mixture. Compositions suitable for direct application or field application generally contain the active compound in an amount substantially between about 0.0001–95%, preferably between about 0.0005–90% by weight, and more preferably between about 0.001–75% by weight of the mixture. The composition can also be stated as a ratio of the compound to the carrier. In the present invention the weight ratio of these materials (active compound/carrier) can vary from 99:1 to 1:4 and more preferably from 10:1 to 1:3.

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a pyridazinone, 45 parts of a synthetic precipitated hydrated silicon dioxide, such as that sold under the trademark Hi-SilR, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex®7.

Dusts are prepared by mixing the pyridazinone, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combatting or controlling pests which compromises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:
1. A dihydropyridazinone and pyridazinone compound having the structure

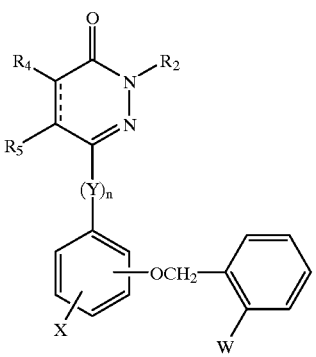

(I)

wherein W is

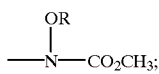

n is 0 or 1;
Y is O, S, $NR_1$, or $R_6$;
the ring bond containing $R_4$ and $R_5$ is a single or double bond;
X is independently selected from hydrogen, halo, $(C_1-C_4)$ alkyl, $(C_1-C_4)$alkoxy and —HC=CH—CH=CH— thereby forming a naphthyl ring;
R is independently selected from $(C_1-C_{12})$alkyl and halo $(C_1-C_{12})$alkyl;
$R_1$ is independently selected from $(C_1-C_{12})$alkyl, $(C_2-C_8)$ alkenyl, phenyl and naphthyl which phenyl or naphthyl may be substituted with up to three substituents selected from the group consisting of halogen, cyano, nitro, trihalomethyl, $(C_1-C_4)$alkyl, $(C_1-C_4)$alkylthio, $(C_1-C_4)$alkylsulfoxide $(C_1-C_6)$alkoxy and halo $(C_1-C_4)$alkyl, excluding phenyl or naphthyl substituted with 2-alkylthio, 2-alkylsulfoxide, or adjacent trinitro, triiodo or tri-tertbutyl moieties;
$R_2$ is independently selected from hydrogen, $(C_1-C_{12})$ alkyl, $(C_1-C_{12})$alkoxy, halo$(C_1-C_{12})$alkyl, halo $(C_1-C_{12})$alkoxy, hydroxy$(C_1-C_{12})$alkyl, $(C_1-C_{12})$ alkoxy$(C_1-C_{12})$alkyl, $(C_1-C_{12})$alkoxycarbonyl $(C_1-C_{12})$alkyl, $(C_2-C_8)$alkenyl, halo$(C_2-C_8)$alkenyl, $(C_3-C_{10})$alkynyl, halo$(C_3-C_{10})$alkynyl, $(C_3-C_7)$ cycloalkyl, $(C_3-C_7)$cycloalkyl$(C_1-C_4)$alkyl, $PO(OR_1)_2$ $(C_1-C_{12})$alkyl, $R_1S(O)_2(C_1-C_{12})$alkyl, $(R_1)_3Si$ $(C_1-C_{12})$alkyl, phenoxy$(C_1-C_{12})$alkyl, naphthyloxy $(C_1-C_{12})$alkyl, phenylcarbonyl$(C_1-C_{12})$alkyl, naphthylcarbonyl$(C_1-C_{12})$alkyl, phenylalkyl, naphthylalkyl, phenylalkenyl, naphthylalkenyl, phenyl, and naphthyl, any of which phenyl or naphthyl may be substituted with up to three substituents selected from the group consisting of halogen, cyano, nitro, trihalomethyl, $(C_1-C_4)$alkyl, $(C_1-C_4)$alkylthio, $(C_1-C_4)$alkylsulfoxide $(C_1-C_6)$alkoxy and halo $(C_1-C_4)$alkyl, excluding phenyl or naphthyl substituted with 2-alkylthio, 2-alkylsulfoxide, or adjacent trinitro, triIodo or tritertbutyl moieties;

$R_4$ and $R_5$ are independently selected from hydrogen, halo, $(C_1-C_8)$alkyl, $(C_1-C_8)$alkoxy, cyano, halo $(C_1-C_{12})$alkyl, $(C_2-C_8)$alkenyl, $(C_3-C_{10})$alkynyl, aryl and aralkyl; and
$R_6$ is $(C_1-C_{12})$ alkyl and $(C_2-C_{12})$ alkenyl.

2. The compound of claim 1 wherein the ring bond between the carbon bonded to $R_4$ and $R_5$ is a double bond.

3. The compound of claim 1 wherein the ring bond between the carbon bonded to $R_4$ and $R_5$ is a single bond.

4. The compounds of claim 2 wherein $R_4$ and $R_5$ are hydrogen, the moiety

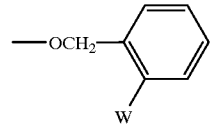

is meta to Y, R is methyl and $R_2$ is selected from the group consisting of $(C_1-C_{12})$alkyl, $(C_2-C_8)$alkenyl, halo$(C_1-C_{12})$ alkyl, phenylalkyl, naphthylalkyl wherein the phenyl and naphthyl rings can be optionally substituted, and halo $(C_2-C_8)$alkenyl.

5. The compound of claim 4 wherein n=0, X is hydrogen and $R_2$ is selected from the group consisting of ethyl, propyl, butyl, vinyl, allyl, chloroethyl, fluoroethyl and substituted benzyl.

6. The compound of claim 5 wherein $R_2$ is selected from halosubstituted benzyl, $(C_{1-C4})$alkyl substituted benzyl, trihalosubstituted benzyl and cyano substituted benzyl.

7. The compound of claim 6 wherein $R_2$ is selected from 2-chlorobenzyl, 3-chlorobenzyl, 4-chlorobenzyl, 2-fluorobenzyl, 3-fluorobenzyl, 4-fluorobenzyl, 2-cyanobenzyl, 3-cyanobenzyl, 4-cyanobenzyl and 4-trifluoromethylbenzyl.

8. The compounds of claim 3 wherein $R_4$ and $R_5$ are hydrogen, the moiety

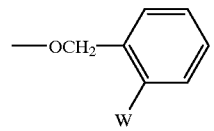

is meta to Y, R is methyl and $R_2$ is selected from the group consisting of $(C_1-C_{12})$alkyl, $(C_2-C_8)$alkenyl, halo $(C_1-C_{12})$alkyl, phenylalkyl, naphthylalkyl wherein the phenyl and naphthyl rings can be optionally substituted, and halo$(C_2-C_8)$alkenyl.

9. The compound of claim 8 wherein n=0, X is hydrogen and $R_2$ is selected from the group consisting of ethyl, propyl, butyl, vinyl, allyl, chloroethyl, fluoroethyl and substituted benzyl.

10. The compound of claim 9 wherein $R_2$ is selected from halosubstituted benzyl, $(C_1-C_4)$alkyl substituted benzyl, trihalosubstituted benzyl and cyano substituted benzyl.

11. The compound of claim 10 wherein $R_2$ is selected from 2-chlorobenzyl, 3-chlorobenzyl, 4-chlorobenzyl, 2-fluorobenzyl, 3-fluorobenzyl, 4-fluorobenzyl, 2-cyanobenzyl, 3-cyanobenzyl, 4-cyanobenzyl and 4-trifluoromethylbenzyl.

12. A fungicidal composition for controlling phytopathogenic fungi which comprises an agronomically acceptable carrier and the compound of claim 1 wherein the ratio of the carrier to the compound is 99:1 to 1:4.

13. The composition of claim 12 wherein the ratio of the agriculturally acceptable carrier to compound is 10:1 to 1:3.

14. A method for controlling phytopathogenic fungi which comprises applying to the locus where control is desired the compound of claim 1 at a rate of from 0.005 to 50 kilograms per hectare.

15. The method of claim 14 wherein the compound of claim 1 is applied at the rate of from 0.025 to 10 kilograms per hectare.

16. A method for controlling insects which comprises applying to the insect's habitat the compound of claim 1 at a rate of 0.005 to 10 kilograms per hectare.

17. The method of claim 16 wherein the compound is applied at a rate of 0.01 to 1 kilogram per hectare.

* * * * *